United States Patent [19]

Sjoerdsma

[11] 4,215,130

[45] Jul. 29, 1980

[54] ANTIHYPERTENSIVE COMPOSITIONS OF N-(2,6-DICHLOROPHENYL)-4,5-DIHYDRO-1H-IMIDAZOL-2-AMINE AND N-(2-CHLOROETHYL)-N-(1-METHYL-2-PHENOXYETHYL)-BENZENEMETHANAMINE

[75] Inventor: Albert Sjoerdsma, Cincinnati, Ohio

[73] Assignee: Richardson-Merrell Inc., Wilton, Conn.

[21] Appl. No.: 802,027

[22] Filed: May 31, 1977

[51] Int. Cl.$^2$ ................ A61K 31/135; A61K 31/415
[52] U.S. Cl. .................................. 424/273 R; 424/330
[58] Field of Search .................. 424/273, 330, 273 R

[56] References Cited

U.S. PATENT DOCUMENTS

| | | | |
|---|---|---|---|
| 2,599,000 | 6/1952 | Kerwin et al. | 260/570.7 |
| 3,236,857 | 2/1966 | Zeile et al. | 260/309.6 |
| 4,022,893 | 5/1977 | Moyer | 424/246 |

OTHER PUBLICATIONS

Wing et al., British Medical Journal 1, 136–138, (1977).
Hansson et al., American Heart Journal 85, 605–610, (1973).
Schmitt et al., European Journal of Pharmacology 14, 98–100, (1971).
Bolme & Fuxe, European Journal of Pharmacology 13, 168–174, (1971).
Bogaievsky, Chem. Abs., vol. 83, 1975, Ab. No. 108506x.
Schmitt, Chem. Abs., vol. 72, 1970, Ab. No. 109390q.
Boissier, Chem. Abs., vol. 68, 1968, Ab. No. 103717x.
Anden, Chem. Abs., vol. 86, 1977, Ab. No. 26041q, (citing European J. Pharm., Oct. 1976, vol. 39).
Delbarre, Chem. Abs., vol. 81, 1974, Ab. No. 130901c.
Tabei, Clin. Pharm. & Therap., vol. 11, 1970, pp. 269–274.
Rubin, New Drugs, M. Dekker, NY, 1978, pp. 59, 65.
Ohkusu, Japan. Circulation J., vol. 35, Oct. 1971, pp. 1175–1181.
Sugimoto, Chem. Abs., vol. 85, 1976, Ab. No. 87361v.
Saito, Chem. Abs., vol. 88, 1978, Ab. No. 115220f.
Iriuchijima, Chem. Abs., vol. 82, 1975, Ab. No. 51543e.

*Primary Examiner*—Anna P. Fagelson
*Attorney, Agent, or Firm*—William J. Stein; Eugene O. Retter; George W. Rauchfuss, Jr.

[57] ABSTRACT

Therapeutic antihypertensive compositions containing N-(2,6-dichlorophenyl)-4,5-dihydro-1H-imidazol-2-amine and N-(2-chloroethyl)-N-(1-methyl-2-phenoxyethyl)benzenemethanamine or their non-toxic, pharmaceutically acceptable salts are described as well as a method of reducing blood pressure in mammals.

6 Claims, No Drawings

ANTIHYPERTENSIVE COMPOSITIONS OF N-(2,6-DICHLOROPHENYL)-4,5-DIHYDRO-1H-IMIDAZOL-2-AMINE AND N-(2-CHLOROETHYL)-N-(1-METHYL-2-PHENOXYETHYL)-BENZENEMETHANAMINE

BACKGROUND OF THE INVENTION

An estimated 23 million Americans, or about 15% of the adult population, have high blood pressure. Of these, approximately one-half are unaware of their condition; of the one-half that are cognizant of their condition, only one-half are receiving drug therapy; and, of those on therapy, only one-half can be considered to be under control. High blood pressure, or hypertension, is the primary cause of more than 60,000 deaths each year and is an underlying cause in more than 1,500,000 heart attacks and strokes occurring each year in the United States. Nearly one-half of these heart attacks and strokes are fatal, while the majority of those victims who do not succumb are restricted in their activity.

Evidence suggests that the sympathetic nervous system plays an important role in ordinary or essential hypertension. Pharmacological agents that block or abolish the sympathetic input to the circulatory system act to lower blood pressure as well as plasma norepinephrine levels. Norepinephrine is a sympathomimetic hormone that acts as a neurotransmitters when released from sympathetic nerve endings in response to nerve impulses. When released, norepinephrine constricts the blood vessels resulting in a rise in blood pressure. The $\alpha$-receptor blocking drug, N-(2-chloroethyl)-N-(1-methyl-2-phenoxyethyl)benzene-methanamine, hereinafter referred to by its generic name, phenoxybenzamine, has been reported to benefit some patients with hypertension. However, its low effectiveness and concomitant side-effects, such as postural hypotension, palpitations and problems with sexual function, have discouraged its use.

The compound N-(2,6-dichlorophenyl)-4,5-dihydro-1H-imidazol-2-amine, hereinafter referred to by its generic name, clonidine, is a potent antihypertensive agent. Considerable evidence suggests that clonidine acts at the $\alpha$-adrenergic receptor sites in the brain to reduce blood pressure. In contrast to phenoxybenzamine, clonidine acts to mimic rather than to block the neurotransmitter norepinephrine at the $\alpha$-adrenergic receptors. Clonidine acts both at the $\alpha$-adrenergic receptors in the blood vessels to raise blood pressure as well as upon $\alpha$-adrenergic receptors on certain neurons in the brain to lower blood pressure. At clinical doses, the latter mode of action usually predominates, resulting in a decrease in sympathetic activity, cardiac output and blood pressure.

Some of the side-effects of clonidine treatment, however, mitigate against its widespread usage, particularly with respect to its use in long-term maintenance therapy of essential hypertension. Thus, drowsiness, sleepiness, lethargy, dry-mouth, constipation, headache and fatigue have all been reported with clonidine treatment. Furthermore, in some patients treated for essential hypertension, the continued administration of high doses of clonidine results in the development of a tolerance with a resulting diminished, antihypertensive effectiveness of the drug, see Wing et al., Br. Med. J. 1, 136-8 (1977). Even more seriously, a sudden interruption or withdrawal of clonidine therapy will, in some instances, precipitate a rebound hypertension or hypertensive crisis, a potential hazard where patient compliance is lacking, see Hansson et al., Am. Heart J. 85, 605-10 (1973).

I have discovered that the conjoint administration of certain combinations of phenoxybenzamine and clonidine actually enhances the antihypertensive effect obtained with clonidine alone, thereby permitting the overall administration of decreased amounts of clonidine to the patient. The administration of decreased amounts of clonidine minimizes some or all of the undesirable effects of the drug, delays the problem of drug tolerance, and reduces the problem of rebound hypertension upon discontinuance of the drug, thereby providing hypertensive patients with increased benefits from this useful drug, not heretofore available.

SUMMARY OF THE INVENTION

This invention relates to novel therapeutic compositions of clonidine and phenoxybenzamine. More particularly, this invention relates to antihypertensive compositions comprising dosage units administered daily comprising from 0.05 to 2.0 milligrams of clonidine and from 1 to 25 milligrams of phenoxybenzamine, or each of their pharmaceutically acceptable salts, in combination with an inert pharmaceutical carrier.

Additionally, this invention relates to a method of lowering the blood pressure of hypertensive mammals which comprises the daily administration of from 0.001 to 0.04 mg/kg of clonidine in combination with from 0.02 to 10.0 mg/kg of phenoxybenzamine.

DETAILED DESCRIPTION OF THE INVENTION

The administration of a combination of an $\alpha$-adrenergic blocking agent, such as phenoxybenzamine, with clonidine to lower blood pressure is clearly contraindicated in the art. Thus, the blood pressure lowering action of clonidine is antagonized by the administration of the $\alpha$-adrenergic receptor blocking drugs piperoxane, see Schmitt et al., Eur. J. Pharmacol. 14, 98-100 (1971) and phenoxybenzamine, see Bolme and Fuxe, Eur. J. Pharmacol. 13, 168-174 (1971). In the latter case, the intravenous administration of from 5 to 10 mg/kg of phenoxybenzamine to anesthetized normotensive cats blocked the blood pressure lowering action of clonidine. Thus, the art clearly teaches that the use of phenoxybenzamine antagonizes or blocks the blood pressure lowering action of clonidine and should not be administered concomitantly therewith.

Surprisingly, I have discovered that the antihypertensive effects of clonidine can actually be enhanced or potentiated, rather than antagonized or blocked, by the concurrent administration of phenoxybenzamine in amounts less than that required to block central $\alpha$-adrenergic receptors. Thus, when clonidine and phenoxybenzamine are concomitantly administered to humans, the antihypertensive effects of clonidine are clearly not antagonized as would have been predicted from the art. Moreover, at the proper dose, in certain individuals the antihypertensive effects of clonidine are enhanced and the rebound effect delayed.

Due to the many contributing factors resulting in essential hypertension in humans, such as stress, mental and emotional factors, and because of the high variability in blood pressure obtained even with the same patient, the hypertensive rat model can best be employed to demonstrate the enhanced antihypertensive effects of phenoxybenzamine and clonidine. Thus, as further illustrated in Examples 5 and 6 below, the administration of clonidine to spontaneously hypertensive rats results in an enhancement or potentiation of the antihypertensive effects of clonidine over and above that due to either clonidine or phenoxybenzamine itself. Whereas the mode of action for this specific combination of drugs is not rigorously understood, it is believed, inter alia, that the amounts of phenoxybenzamine employed herein may serve to selectively inhibit the known pressor effects of clonidine due to its action upon the peripheral α-adrenergic receptor sites, enabling clonidine to exert a more dramatic anti-hypertensive effect by virtue of its unhampered action in the brain.

Accordingly, the present invention relates to anti-hypertensive compositions in dosage unit form containing clonidine in combination with phenoxybenzamine. These compositions serve to ameliorate some of the adverse side-effects of clonidine therapy and prevent the loss of drug effectiveness upon long-term clonidine administration. Moreover, the inhibition by phenoxybenzamine of the peripheral α-adrenergic receptor sites, serves to minimize the peripheral vasoconstrictor action of clonidine, thereby alleviating hypertensive rebound after sudden discontinuance or withdrawal of clonidine therapy.

Clonidine is described and can be prepared in accordance with the procedures set forth in U.S. Pat. No. 3,236,857. Phenoxybenzamine can be obtained and prepared in accordance with the teachings of U.S. Pat. No. 2,599,000.

The expression "pharmaceutically acceptable salts" as used herein, encompasses the acid addition salts of either clonidine and/or phenoxybenzamine and includes both the non-toxic inorganic and organic acid addition salts of the base compounds. Illustrative inorganic acids which form suitable salts include hydrochloric, hydrobromic, sulfuric and phosphoric acids and acid metal salts such as sodium monohydrogen orthophosphate and potassium hydrogen sulfate. Illustrative organic acids which form suitable salts include the mono, di and tricarboxylic acids, for example, acetic, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Preferably, the hydrochloride salt of clonidine and phenoxybenzamine is employed for reasons of pharmaceutical stability and pharmacological compatibility.

The novel compositions containing clonidine and phenoxybenzamine can be administered in a variety of ways and in various different dosage unit forms, e.g., oral compositions such as tablets, capsules, lozenges, elixirs, emulsions, clear liquid solutions and suspensions; and parenteral compositions such as intramuscular, intravenous or intradermal preparations. The amount of active ingredient contained in each dosage unit form will, of course, vary widely according to the particular dosage unit employed, the period of treatment, the age and sex of the patient treated, and the nature of the particular type of hypertension being treated. Thus, a particular dosage unit may contain from as little as 1 mg to slightly over 150 mg of the combined active ingredients in addition to any pharmaceutical excipients that may be contained therein. Preferably, the total amount of active ingredients ranges from 1 to 50 mg per dosage unit.

The combination of clonidine and phenoxybenzamine is most advantageously administered as a pharmaceutical composition in conjunction or admixture with additional organic or inorganic pharmaceutical excipients. Suitable solid excipients include inert diluents, for example, calcium carbonate, sodium carbonate, lactose, calcium phosphate or sodium phosphate; granulating and disintegrating agents, as for example, maize starch or alginic acid; binding agents, as for example various starches, gelatin, lactose or acacia mucilage, and lubricating agents, such as magnesium stearate, stearic acid or talc. Suitable liquid excipients include water and alcohols, such as ethanol, benzyl alcohol and the polyethylene alcohols, either with or without the addition of a surfactant. In general, the preferred liquid excipients, particularly for injectable preparations include water, saline solution, dextrose and glycol solutions such as aqueous propylene glycol or an aqueous solution of polyethylene glycol. Liquid preparations to be used as sterile injectable solutions will ordinarily contain from about 0.1% to about 25% by weight and preferably from about 0.1% to about 10% by weight of the active ingredients in the solution.

A preferred method of administration for the hypotensive compositions described herein is oral, either in a solid dose form such as a tablet or capsule, or in a liquid dose form such as an elixir, suspension, emulsion or syrup. Ordinarily, the active ingredient comprises from about 0.5% to about 10% by weight of an oral composition. In such compositions the pharmaceutical carrier is generally aqueous in nature, as for example, aromatic water, a sugar-based syrup or a pharmaceutical mucilage. Suspending agents may be added as well as agents to control the viscosity, as for example, magnesium aluminum silicate or carboxymethylcellulose. Buffers, preservatives, emulsifying agents and other excipients can also be added.

Formulations for oral use may be presented as hard or soft shell gelatin capsules containing only the active ingredients, or containing the active ingredients in admixture with a solid diluent, as for example lactose, sorbitol, calcium carbonate, calcium phosphate or kaolin.

Tablets containing clonidine and phenoxybenzamine can be prepared by the conventional wet granulation method which consists of moistening the dry powders, with or without the addition of an adhesive substance, until the whole is converted into crumbly mass. Well-known moistening agents, such as water or other solvents can be employed. In addition, it is a common practice to add a substance such as gelatin, starch or gum acacia in order to assist in granulating these materials. The granules so prepared can be lubricated by dusting or dry blending with a lubricant such as talc or zinc stearate and compressed in the usual manner known to the art.

Alternatively, a dry granulating process can be employed which consists of pre-compressing the active ingredients and/or diluents as dry powders into over-sized tablets or "slugs". These over-sized tablets or "slugs" are broken into granules, screened, lubricated, and compressed in a tablet machine to form tablets of the desired size and shape. The resulting tablets may be uncoated or they may be coated by known techniques to delay disintegration in the gastro-intestinal tract and thereby provide a sustained action over a longer period of time. Tablets can be prepared in which clonidine is separately incorporated as a sustained release formulation. Such a sustained release tablet need be administered only once daily, thereby maximizing patient compliance.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a nonionic surfactant having a hydrophile-lipophile balance (HLB) of from about 12 to about 17. The quantity of surfactant in such formulations ranges from about 1% to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising liquid pharmaceutical excipients previously mentioned.

According to a further feature of this invention, there is provided a method for lowering the blood pressure in hypertensive mammals which comprises administering concomitantly an effective amount of clonidine with phenoxybenzamine, preferably as one of the compositions in dosage unit form heretofore described. Illustrative of the term "mammals" are such species as mice, rats, guinea pigs, rabbits, ferrets, dogs, cats, cows, horses and primates including man. Use of the expression "administering concomitantly" indicates that the active ingredients are either administered simultaneously, by the same or different routes, or they are administered at an appropriate time interval so that the patient derives the maximum advantage from the combined therapy.

The pharmaceutical compositions are administered to animals at a daily dose ranging from about 0.001 to 0.04 mg/kg of clonidine, and from about 0.02 to 10 mg/kg of phenoxybenzamine per body weight. Preferably, a dose of from about 0.001 to 0.01 mg/kg of clonidine, and from about 0.02 to 2.0 mg/kg of phenoxybenzamine is administered to achieve an antihypertensive effect in humans with severe hypertension. Mild to moderate forms of hypertension can be treated with smaller doses or at less frequent intervals. Humans are much more sensitive to the α-adrenergic blocking action of phenoxybenzamine. Thus, an adequate blockage of α-adrenergic receptors in humans can be obtained at a daily dose of phenoxybenzamine ranging from 0.02 to 2.0 mg/kg.

Preferably, the combination of active ingredients is orally administered as a tablet or a capsule one to four times daily. Still more preferably, the active ingredients are proportionately increased in these dosage unit forms so that they can be administered two or three times per day.

The invention is more particularly illustrated, but not limited by the following specific Examples.

EXAMPLE 1

Preparation of a Tablet Formulation

One thousand tablets suitable for oral use are prepared in accordance with the following formulation.

|     |                                                                                    | Gm.   |
| --- | ---------------------------------------------------------------------------------- | ----- |
| (a) | N-(2,6-dichlorophenyl)-4,5-dihydro-1H-imidazol-2-amine hydrochloride               | 0.2   |
| (b) | N-(2-chloroethyl)-N-(methyl-2-phenoxyethyl) benzenemethanamine hydrochloride       | 10.0  |
| (c) | Dicalcium phosphate                                                                | 150.0 |
| (d) | Methylcellulose, U.S.P. (15 cps)                                                   | 6.5   |
| (e) | Talc                                                                               | 20.0  |
| (f) | Calicum Stearate                                                                   | 2.5   |

The N-(2,6-dichlorophenyl)-4,5-dihydro-1H-imidazol-2-amine, N-(2-chloroethyl)-N-(1-methyl-2-phenoxyethyl)benzene-methanamine and dicalcium phosphate are mixed well as a dry powder. The resulting powder is granulated using a 7.5% aqueous solution of methylcellulose, passed through a No. 8 screen and carefully dried. The dried granules prepared in this fashion are passed through a No. 12 screen, lubricated with the remaining talc and calcium stearate, and compressed into tablets. Each tablet contains 0.2 mg of clonidine and 10 mg of phenoxybenzamine and is suitable for administration b.i.d. to q.i.d.

EXAMPLE 2

Preparation of a Capsule Formulation

One thousand two-piece hard shell capsules suitable for oral use are prepared using the following ingredients.

|     |                                                                                 | Gm.   |
| --- | ------------------------------------------------------------------------------- | ----- |
| (a) | N-(2,6-dichlorophenyl)-4,5-dihydro-1H-imidazol-2-amine hydrochloride            | 0.2   |
| (b) | N-(2-chloroethyl)-N-(1-methyl-2-phenoxyethyl)benzenemethanamine hydrochloride   | 10.0  |
| (c) | Lactose, U.S.P.                                                                 | 100.0 |
| (d) | Starch, U.S.P.                                                                  | 10.0  |
| (e) | Talc, U.S.P.                                                                    | 5.0   |
| (f) | Calcium Stearate                                                                | 1.0   |

All of the finely powdered materials are mixed dry until uniformly dispersed and then filled into hard-shelled gelatin capsules of the appropriate size.

In a similar fashion, one-piece soft gelatin capsules can be prepared in which the above formulation is granulated, slugged or directly compressed into a rotary die or plate mold in which the capsule is to be formed. Alternatively, the above excipients can be omitted and the active ingredients dispensed as a powder directly into the capsule.

Each capsule contains 0.2 mg of clonidine and 10 mg of phenoxybenzamine and is suitable for oral administration, b.i.d. to q.i.d.

EXAMPLE 3

Preparation of a Parenteral Solution

A Sterile aqueous solution is prepared as follows.

|     |                                                                                      | Gm.  |
| --- | ------------------------------------------------------------------------------------ | ---- |
| (a) | N-(2,6-dichlorophenyl)-4,5-dihydro-1H-imidazol-2-amine hydrochloride                 | 0.3  |
| (b) | N-(2-chloroethyl)-N-(1-methyl-2-phenoxyethyl)benzenemethanamine hydrochloride         | 15.0 |
| (c) | Sodium chloride                                                                      | 0.9  |
| (d) | Methylparaben                                                                        | 0.18 |
| (e) | Propylparaben                                                                        | 0.02 |
| (f) | Water for injection, q.s. to 1000 ml                                                 |      |

The above ingredients are dissolved in the water and sterilized by filtration. Each ml of solution contains 0.3 mg of clonidine and 15 mg of phenoxybenzamine and is suitable for intravenous injection b.i.d.

EXAMPLE 4

Preparation of a Slow-Release Layered Tablet

One thousand layered tablets, comprising a slow release layer of clonidine and a rapid release layer of phenoxybenzamine are prepared as follows.

|     |                                                                      | Gm.   |
| --- | -------------------------------------------------------------------- | ----- |
|     | Slow Release Layer                                                   |       |
| (a) | N-(2,6-dichlorophenyl)-4,5-dihydro-1H-imidazol-2-amine hydrochloride | 0.4   |
| (b) | Hydroxypropyl Methylcellulose (4000 cps)                             | 100.0 |
| (c) | Mannitol                                                             | 200.0 |
| (d) | Corn Starch                                                          | 6.0   |
| (e) | Zinc Stearate                                                        | 3.6   |
|     | Rapid Release Layer                                                  |       |
| (f) | N-(2-chloroethyl)-N-(1-methyl-2-phenoxyethyl)benzenemethamine hydrochloride | 20.0 |
| (g) | Microcrystalline cellulose                                           | 150.0 |
| (h) | Starch                                                               | 150.0 |

Using a suitable mixer, the N-(2,6-dichlorophenyl)-4,5-dihydro-1H-imidazol-2-amine hydrochloride, mannitol and hydroxypropyl methylcellulose are mixed well via geometric dilution. The mixture is mixed in a Fitzmill equipped with a No. 000 screen and granulated using a 5% starch paste prepared by adding the corn starch to approximately 115 ml of water. Additional water is added as required to make a suitable granulation. The resulting granulation is wet-screened using a No. 2 screen and tray dried at 40° C. to 50° C. for 8 to 12 hours. The dried granulation is ground and passed through a No. 10 screen. Zinc stearate, which has passed through a No. 20 screen is added to the granulation, mixed well and the resulting slow release granulation reserved for tablet compression.

The N-(2-chloroethyl)-N-(1-methyl-2-phenoxyethyl)-benzenemethanamine hydrochloride is milled, if necessary, to obtain a powder having the majority of particles in the range of 10 to 150 microns in size. The milled powder, microcrystalline cellulose and starch are mixed well in a Fitzmill equipped with No. 000 screen and the resulting rapid release mixture reserved for tablet compression.

Using a suitable layer press, such as the Manesty Layer Press, the slow release granulation is added to the adjusted die cavity to provide a layer with a weight of 310 mg. The granulation is lightly tamped by subjecting to a precompression stroke and the rapid release layer added to provide a layer having a weight of 320 mg. The final compression pressure is adjusted to provide a suitable tablet with a total weight of 630 mg. Each tablet contains 0.4 mg of clonidine and 20 mg of phenoxybenzamine, and can be administered once a day to effect maximum patient compliance.

EXAMPLE 5

The following Example illustrates the threshold dose of phenoxybenzamine required for its α-adrenergic blocking action in inhibiting the norepinephrine pressor response.

Three groups of female spontaneously hypertensive rats (10–11 months of age, 6 rats per group) are intraperitoneally treated with either propylene glycol (1 cc/kg) as a control, or phenoxybenzamine hydrochloride. The phenoxybenzamine is dissolved in propylene glycol in sufficient concentration to be administered at a dose of 1 cc/kg. One hour later the animals are anesthetized with urethan (780 mg/kg i.v.) and their left common carotid arteries and right jugular veins are cannulated. Arterial blood pressure is recorded from the carotid artery by means of an arterial pressure transducer.

Two hours after pretreatment with phenoxybenzamine, or propylene glycol in the case of the control animals, the animals are challenged with norepinephrine bitartrate, administered intravenously (0.3 micrograms/kg). The norepinephrine bitartrate (0.3 micrograms/kg) is dissolved in saline solution to which 0.01% of ascorbic acid is added in order to retard oxidative degradation of norepinephrine. The following blood pressures expressed in mm of Hg are observed in response to the norepinephrine challenge.

| Control animals              | 31.06 ± 2.55 mm |
| ---------------------------- | --------------- |
| Phenoxybenzamine treatment   |                 |
| 10 mg/kg                     | 22.81 ± 5.73 mm |
| 30 mg/kg                     | 12.51 ± 2.36 mm |

These results indicate that in the spontaneous hypertensive rat a dose of 10 mg/kg of phenoxybenzamine is a threshhold dose to achieve peripheral α-adrenergic receptor blockade.

EXAMPLE 6

The following Example illustrates the enhanced antihypertensive effects obtained with clonidine in combination with an insufficient amount of phenoxybenzamine to act as a central α-adrenergic blocking agent.

Two distinct groups of male spontaneously hypertensive rats (8–9 months of age, 6 rats per group) are placed in plexiglass housing chambers equipped with pressure cuffs and photocell transducers connected to a Sphygmomanometer via a photopulse amplifier suitable for measuring blood pressure. Male animals are preferred because of their larger size, making blood pressure measurements more accurate and reliable.

One group of animals are administered propylene glycol at a dose of 1 cc/kg, whereas the remaining two groups of animals were administered phenoxybenzamine hydrochloride at a dose of 10 mg/kg. Two hours later, the one group of animals receiving propylene glycol and one of the two groups of animals receiving phenoxybenzamine are administered clonidine hydrochloride (i.p.) at a dosage of 30 micrograms/kg. At the same time, the remaining group of phenoxybenzamine pretreated animals are administered an equivalent volume of saline solution. All administrations are effected by the intraperitoneal route of administration. The following blood pressures are recorded one hour later. Blood pressures are expressed in mm of Hg.

Control animals: 165±4.9
Phenoxybenzamine (10 mg/kg): 162±10
Clonidine (0.03 mg/kg): 149±8.6
Phenoxybenzamine (10 mg/kg) in combination with clonidine (0.03 mg/kg): 100±6.3

The above data indicate that whereas the amount of phenoxybenzamine administered is in and of itself insufficient to produce an antihypertensive effect, the same amount of phenoxybenzamine in combination with clonidine produces an additional 30% decrease in blood pressure over that obtained with clonidine alone.

I claim:

1. An antihypertensive composition in dosage unit form comprising from 0.05 to 2 mg of N-(2,6-dichlorophenyl)-4,5-dihydro-1H-imidazol-2-amine and from 1 to 25 mg of N-(2-chloroethyl)-N-(1-methyl-2-phenoxyethyl)benzenemethanamine having an enhanced antihypertensive effect, or each of their pharmaceutically acceptable salts, and a pharmaceutically acceptable carrier.

2. A composition according to claim 1 in which said dosage unit form is a tablet.

3. A method of lowering the blood pressure in hypertensive mammals in need thereof which comprises the administration to said mammals of from 0.001 to 0.04 mg/kg of N-(2,6-dichlorophenyl)-4,5-dihydro-1H-imidazol-2-amine in combination with from 0.02 to 10 mg/kg of N-(2-chloroethyl)-N-(1-methyl-2-phenoxyethyl)benzenemethanamine so as to produce an enhanced antihypertensive effect.

4. A method according to claim 3 wherein the N-(2,6-dichlorophenyl)-4,5-dihydro-1H-imidazol-2-amine is administered at a dosage of from 0.001 to 0.01 mg/kg and the N-(2-chloroethyl)-N-(1-methyl-2-phenoxyethyl)benzenemethanamine is administered at a dosage of from 0.02 to 0.5 mg/kg.

5. A method according to claim 4 in which the mammals are human.

6. A method of lowering the blood pressure in hypertensive mammals in need thereof which comprises the administration to said mammals of 0.03 mg/kg of N-(2,6-dichlorophenyl)-4,5-dihydro-1H-imidazol-2-amine in combination with 10 mg/kg of N-(2-chloroethyl)-N-(1-methyl-2-phenoxyethyl)benzenemethanamine so as to produce an antihypertensive effect.

* * * * *